United States Patent
Dickneite

(10) Patent No.: US 8,580,737 B2
(45) Date of Patent: *Nov. 12, 2013

(54) SYNERGISTIC THERAPEUTIC USE OF PROTHROMBIN COMPLEX CONCENTRATES WITH FVIII CONCENTRATES

(75) Inventor: Gerhard Dickneite, Marburg (DE)

(73) Assignee: CSL Behring GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/611,419

(22) Filed: Sep. 12, 2012

(65) Prior Publication Data

US 2013/0005657 A1 Jan. 3, 2013

Related U.S. Application Data

(63) Continuation of application No. 12/520,773, filed as application No. PCT/EP2007/011099 on Dec. 18, 2007.

(30) Foreign Application Priority Data

Dec. 22, 2006 (EP) .................................. 06026748

(51) Int. Cl.
- A61K 38/36 (2006.01)
- A61K 38/00 (2006.01)
- A61P 7/02 (2006.01)
- A61P 7/00 (2006.01)
- C07K 14/745 (2006.01)

(52) U.S. Cl.
USPC ........................................ 514/13.7; 514/13.5

(58) Field of Classification Search
None
See application file for complete search history.

(56) References Cited

U.S. PATENT DOCUMENTS

| | | | |
|---|---|---|---|
| 4,503,039 A | 3/1985 | Kotitschke | |
| 4,883,598 A | 11/1989 | Riethorst | |
| 5,543,502 A | 8/1996 | Nordfang | |
| 5,866,122 A | 2/1999 | Turecek | |
| 6,051,434 A | 4/2000 | Exner | |
| 6,737,405 B2 | 5/2004 | Roemisch | |
| 6,831,086 B1 | 12/2004 | Bernhardt | |
| 7,795,399 B2 | 9/2010 | Eibl | |
| 8,394,768 B2 * | 3/2013 | Dickneite | 514/13.7 |
| 2010/0093607 A1 * | 4/2010 | Dickneite | 514/8 |

FOREIGN PATENT DOCUMENTS

| | | |
|---|---|---|
| CA | 2156991 A1 | 2/1996 |
| EP | 0 700 684 A2 | 3/1996 |
| EP | 0 796 623 A2 | 9/1997 |
| WO | WO 2004/054607 | 7/2004 |

OTHER PUBLICATIONS

Nielsen et al. Actac Anaesthesiol Scand, Effects of coagulation factor deficiency on plasma coagulation kinetics determined via thromelastography®: critical roles of fibrinogen and factors II, VII, X and XII. Feb. 2005, vol. 49, pp. 222-231.*
CSL Behring. Bleeding Disorders. Accessed online Jun. 22, 2013 at http://www.cslbehring.com/products/bleeding-disorders-product-list.htm , 2 pages.*
Ansell J., et al., "The Pharmacology and Management of the Vitamin K Antagonists: The Seventh ACCP Conference on Antithrombotic and Thrombolytic Therapy," Chest 126: 204S-233S (2004).
Brass, L.F., "Thrombin and Platelet Activation", Chest 124: 18S-25S (2003).
Davie, E.W., et al., "An overview of the structure and function of thrombin," Semin. Thromb. Hemost. 32 Suppl 1:3-15 (2006) (abstract only).
Patrono, C. "Aspirin: new cardiovascular uses for an old drug," Am J. Med 110(1A):62S-65S (2001) (abstract only).
Preston et al., "Rapid reversal of oral anticoagulation with warfarin by a prothrombin complex concentrate (Beriplex): efficacy and safety in 42 patients," British Journal of Haematology 116: 619-624 (2002).
Dickneite et al., "Development of an anti-bleeding agent for recombinant hirudin induced skin bleeding in the pig," Thromb Haemost 809(1): 192-198 (1998).
European Search Report from the European Patent Office for corresponding European Application No. 06 02 6748, (mailing date Jul. 9, 2007).
Brackmann et al.; "Massive Factor-VIII Infusion in Haemophiliac with Factor-VIII Inhibitor, High Responder", The Lancet, vol. 2, No. 8044, XP008080612, p. 933, (1977).
Scheibel et al.; "Long-Term High Dose Factor-VIII Treatment of 3 Haemohiliacs with Factor-VIII Inhibitor", Scand J Haematol, vol. 34, No. 5, XP008080497, pp. 378-384, (1985).
Leggett et al.; "Elective Cardiac Operation in a Patient with Severe Hemophilia and Acquired Factor-VIII Antibodies", J Thorac Cardiovasc Surg, vol. 87, No. 4, XP008080498, pp. 556-560, (1984).
Hardy et al.; "Massive Transfusion and Coagulopathy: Pathophysiology and Implications for Clinical Management", Canadian Journal of Anesthesia, vol. 51, No. 4, pp. 293-310, (2004).
Ruggeri; "Von Willebrand Factor", Current Opinion in Hematology, vol. 10, pp. 142-149, (2003).

(Continued)

Primary Examiner — Marcela M Cordero Garcia
(74) Attorney, Agent, or Firm — Finnegan, Henderson, Farabow, Garrett & Dunner, LLP

(57) ABSTRACT

The field of the invention is the treatment of acquired bleeding, a clinical condition associated with severe traumatic, peri- or post-operative bleeding. A novel treatment is proposed in which synergistic pro-coagulatory properties of Prothrombin Complex Concentrates (PCC) together with medicaments comprising FVIII and/or vWF are exploited.

20 Claims, 1 Drawing Sheet

(56) References Cited

OTHER PUBLICATIONS

Monroe et al.; "Platelets and Thrombin Generation", Arterioscler Thromb Vasc Biol., vol. 22, 1381-1389, (2002).
Morrissey; "Tissue Factor: An Enzyme Cofactor and a True Receptor", Thromb Haemost, vol. 86, pp. 66-74, (2001).
Hiippala et al.; "Hemostatic Factors and Replacement of Major Blood Loss with Plasma-Poor Red Cell Concentrates", Anesth Analg, vol. 81, pp. 360-365, (1995).
Hiippala; "Replacement of Massive Blood Loss", Vox Sanguinis, vol. 74, Suppl. 2, pp. 399-407, (1998).
McLoughlin et al.; "Profound Normovolemic Hemodilution: Hemostatic Effects in Patients and in a Porcine Model", Anesth Analg, vol. 83, pp. 459-465, (1996).
Sheiner et al.; "Obstetric Risk Factors and Outcome of Pregnancies Complicated with Early Postpartum Hemorrhage: A Population-Based Study", The Journal of Maternal-Fetal and Neonatal Medicine, vol. 18, No. 3, pp. 149-154, (2005).
Innerhofer et al.; "The Effects of Perioperatively Administered Colloids and Crystalloids on Primary Platelet-Mediated Hemostasis and Clot Formation", Anesth Analg, vol. 95, pp. 858-865, (2002).
Rohrer; "Effect of Hypothermia on the Coagulation Cascade", Critical Care Medicine (Williams & Wilkins), vol. 20, No. 10, pp. 1402-1405, (1992).
Martini et al.; "Independent Contributions of Hypothermia and Acidosis to Coagulopathy in Swine", The Journal of Trauma: Injury, Infection, and Critical Care, vol. 58, No. 5, pp. 1002-1010, (2005).
Mikhail; "The Trauma Triad of Death: Hypothermia, Acidosis, and Coagulopathy", AACN Clinical Issues, vol. 10, No. 1, pp. 85-94, (1999).
Cosgriff et al.; "Predicting Life-Threatening Coagulopathy in the Massively Transfused Trauma Patient: Hypothermia and Acidoses Revisited", The Journal of Trauma: Injury, Infection, and Critical Care, vol. 42, No. 5, pp. 857-862, (1997).
Vorweg et al.; "Management of Fulminant Fibrinolysis During Abdominal Aortic Surgery", Journal of Cardiothoracic and Vascular Anesthesia, vol. 15, No. 6, pp. 764-767, (2001).
Spivey et al.; "Therapeutic Approaches in Trauma-Induced Coagulopathy", Minerva Anestesiol, vol. 71, No. 6, pp. 281-289, (2005).
Spahn; "Strategies for Transfusion Therapy", Best Practice & Research Clinical Anaesthesiology, vol. 18, No. 4, pp. 661-673, (2004).
Stanworth et al.; "Is Fresh Frozen Plasma Clinically Effective? A Systematic Review of Randomized Controlled Trials", British Journal of Haematology, vol. 126, pp. 139-152, (2004).
Bux; "Transfusion-Related Acute Lung Injury (TRALI): A Serious Adverse Event of Blood Transfusion", Vox Sanguinis, vol. 89, pp. 1-10, (2005).
Fries et al.; "Efficacy of Fibrinogen and Prothrombin Complex Concentrate Used to Reverse Dilutional Coagulopathy—A Porcine Model", British Journal of Anaesthesia, pp. 1-8, (Aug. 1, 2006).
Schulman et al.; "Anticoagulants and Their Reversal", Transfusion Medicine Reviews, vol. 21, No. 1, pp. 37-48, (2007).
Holcomb; "Use of Recombinant Activated Factor VII to Treat the Acquired Coagulopathy of Trauma", The Journal of Trauma: Injury, Infection, and Critical Care, vol. 58, No. 6, pp. 1298-1303, (2005).

Habermann et al.; "Management of Haemophilic Patients with Inhibitors in Major Orthopaedic Surgery by Immunadsorption, Substitution of Factor VIII and Recombinant Factor Vila (NovoSeven®): A Single Centre Experience", Haemophilia, vol. 10, pp. 705-712, (2004).
Fickenscher; "Analysis of Individual Coagulation Factors", Thomas L. Clinical Laboratory Diagnostics, T-H Books, Frankfurt, Germany, Chapter 17.14-17.16, pp. 607-613, (1998).
Frokjaer et al.; "Pharmaceutical Formulation Development of Peptides and Proteins", European Journal of Pharmaceutics and Biopharmaceutics, vol. 50, p. 329, (2000).
Kibbe; "Handbook of Pharmaceutical Excipients", Book Reviews, Journal of Controlled Release, vol. 71, Third Edition, Pharmaceutical Press, pp. 352-353, (2001).
International Search Report from the European Patent Office for International Application No. PCT/EP2007/011099, (mailing date Jun. 4, 2008).
Dickneite et al.: "Reduction of R-Hirudin Induced Bleeding in Pigs by the Administration of Von Willebrand Factor", Platelets, vol. 7, pp. 283-290, (1996).
Berndt et al.: "The Vascular Biology of the Glycoprotein Ib-IX-V Complex", Thromb Haemost, vol. 86, pp. 178-188, (2001).
Mahla et al.; "Thromboelastoography for Monitoring Prolonged Hypercoagulabilty After Major Abdominal Surgery", Anesth Analg, vol. 92, pp. 572-577, (2001).
Martinowitz at al.; "Intravenous rFVIIa Administered for Hemorrhage Control in Hypothermic Coagulopathic Swine with Grade V Liver Injuries", J Trauma, vol. 50, No. 4, pp. 721-729, (2001).
Prevost et al.; "Contact-Dependent Signaling During the Late Events of Platelet Activation", J Thromb Haemost, vol. 1, pp. 1613-1627, (2003).
Innerhofer et al.; "Monitoring of Perioperative Dilutional Coagulopathy Using the ROTEM Analyzer: Basic Principles and Clinical Examples", Transfus Med Hemother, vol. 31, pp. 244-249, (2004).
Coughlin; "Protease-Activated Receptors in Hemostasis, Thrombosis and Vascular Biology", J Thromb Haemost, vol. 3, pp. 1800-1814, (2005).
Dahlback et al.; "Regulation of Blood Coagulation by the Protein C Anticoagulant Pathway", Arterioscler Thromb Vasc Biol., vol. 25, pp. 1311-1320, (2005).
Fries et al,; "Effect of Fibrinogen on Reversal of Dilutional Coagulopathy: A Porcine Model", British Journal of Anaesthesia, vol. 95, No. 2, pp. 172-177, (2005).
Heindl et al.; Hochdosierte Fibrinogengabe Zur Akuttherapie Von Gerinnungsstörungen Bei Perioperativer Massiytransfusion, Anaesthesist, vol. 54, pp. 787-790, (2005).
Klemcke et al.; "Effect of Recombinant FVIIa in Hypothermic, Coagulopathic Pigs with Liver Injuries", J Trauma, vol. 59, pp. 155-161, (2005).
Pusateri et al.; "Effects of Increasing Doses of Activated Recombinant Factor VII on Haemostatic Parameters in Swine", Thromb Haemost, vol. 93, pp. 275-283, (2005).
Dickneite; "Prothrombin Complex Concentrate Versus Recombinant Factor VIIa for Reversal of Coumarin Anticoagulation", Thrombosis Research, accepted May 23, 2006, 9 pages (2006).
Hardy et al.; "Massive Transfusion and Coagulopathy: Pathophysiology and Implications for Ciinical Management", Can J. Anesth, vol. 53, No. 6, pp. S40-S58, (2006).

* cited by examiner

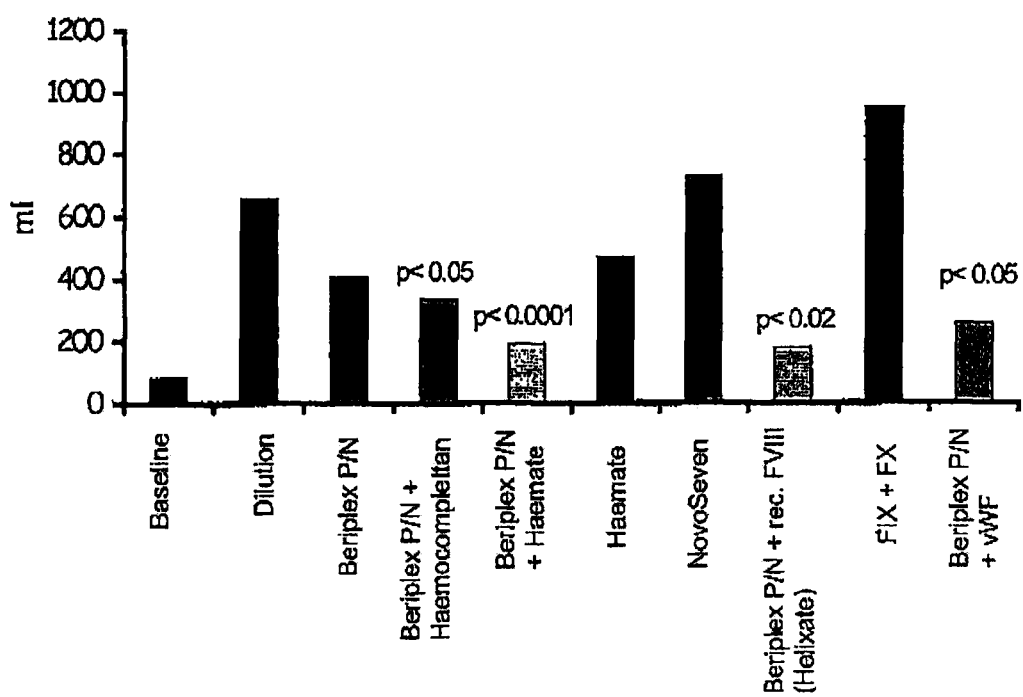

SYNERGISTIC THERAPEUTIC USE OF PROTHROMBIN COMPLEX CONCENTRATES WITH FVIII CONCENTRATES

This is a continuation of application Ser. No. 12/520,773, with §371(c) date Jun. 22, 2009, which is a national stage filing under 35 U.S.C. §371 of International Application No. PCT/EP2007/011099, filed on Dec. 18, 2007, and claims the benefit of priority of European Application No. 06026748.1, filed on Dec. 22, 2006. All of these applications are incorporated herein by reference in their entirety.

The field of the invention is the treatment of acquired bleeding, a clinical condition associated with severe traumatic, peri- or postoperative bleeding. A novel treatment is proposed in which synergistic procoagulatory properties of Prothrombin Complex Concentrates (PCC) together with medicaments comprising FVIII and/or vWF are exploited.

Bleeding as a result of an acquired coagulopathy without an underlying genetic disorder can occur in a variety of clinical constellations. Trauma, peri- or postoperative hemorrhage or anticoagulant overdose can impair the coagulation system. In severe cases coagulopathy is associated with massive blood loss, which needs to be corrected by volume replacement and/or erythrocyte transfusion. Dilution of the functional elements of the coagulation system leads to an elevated bleeding risk. Besides surgical wound closing, restitution of the patient's impaired hemostatic potential is mandatory (Hardy, 2006). Hemostasis is a complex system to prevent the loss of circulating blood. Its main elements are the plasmatic coagulation factors and the circulating platelet pool. The initial event after an injury is the binding of the platelet to the newly exposed subendothelial collagen via its GPIb receptor. This binding is mediated by von Willebrand factor (vWF), a large multimeric protein. VWF has a binding site (A1) for the platelet GPIb receptor, the A3 domain is responsible for the binding to collagen (Ruggeri, 1993). The exposed tissue factor in the subendothelium binds circulating FVII and activates the extrinsic clotting systems by forming activated FVIIa in a presently unknown fashion (Morrissey, 2001). The TF/FVIIa complex activates Factor X to FXa to form a small amount of thrombin. This initial thrombin activates platelets at the site of injury and also the coenzymes FV and FVIII to FVa and FVIIIa, respectively. FXa then binds to the activated platelet where it is converted to FXa by the FIXa/FVIIIa complex. The platelet bound FXa/Va complex converts prothrombin into thrombin and thus mediates the thrombin burst (Monroe et al., 2002). A dilutional coagulopathy is caused by consumption, dilution and losses and affects all aspects of coagulation: The enzymes and proenzymes of the coagulation cascade, fibrinogen and the thrombocytes (Hiippala et al., 1995, Hiippala 1998). As erythrocytes also contribute to hemostasis a decrease of the hematocrit also impairs hemostasis (McLoughlin et al., 1996, Sheiner, 2005). The use of colloids is also known to lead to decreased fibrin polymerization (Innerhofer et al., 2002). Hypothermia has been shown to impair the coagulation as shown in human plasma at different temperatures (Rohrer, 1992). Martini et al. (2005) demonstrated in a preclinical study that hypothermia caused a delay in the thrombin generation. Together with acidosis, hypothermia and coagulopathy form the "lethal trial" of trauma (Mikhail, 1999), a life-threatening coagulopathy develops in the affected patients (Cosgriff et. al, 1997). Activation of the fibrinolytic system might aggravate the situation by the consumption of fibrinogen and fibrin (Vorweg et al., 2001).

The substitution with coagulation factors and cellular elements as erythrocytes and platelets is mandatory to restore the hemostatic balance (Spivey, 2005, Spahn, 2004). The widespread use of fresh frozen plasma (FFP) to correct a coagulopathy is in contrast to the little evidence for effectiveness in the published literature (for review see Stanworth, 2004). The use of FFP is sometimes associated with the development of transfusion-related acute lung injury (TRALI, Bux, 2005). Cryoprecipitate from frozen plasma is used widely in this setting. Based on the poor efficacy and safety concerns, the search for new concepts to overcome a dilutional coagulopathy, therefore remains a clinical challenge.

The invention is based on the use of PCC in this clinical setting. PCC in combination with various coagulation factors has been proposed earlier as an antidote against different anticoagulants e.g. against hirudin (EP 0700684). Also pharmaceutical compositions comprising at least 2 highly purified components selected from the group consisting of factors II, V, Va, X and Xa optionally in combination with other coagulation factors have been disclosed for the treatment of hemophilia A inhibitor patients (EP0796623).

In contrast to the above mentioned PCCs which comprise non-activated coagulation factors FII, FVII, FIX and FX, in the clinical setting also activated PCCs are used. Examples of those activated PCCs are FEIBA® (Immuno-Baxter) and Autoplex® (Hyland). These activated PCCs comprise the coagulation factors FII, FVII, FIX and FX in activated form. The use of activated PCCs carries the inherent risk of prothrombotic side effects, which makes the use of non-activated PCCs favourable.

In a model of dilutional coagulopathy resulting from intended blood loss and fluid replacement recently a combination of PCC and fibrinogen was found to be beneficial (Fries et al., 2006).

However in view of considerable morbidity and mortality caused by acquired coagulopathy there is a high clinical interest and strong incentive to further increase the efficacy of treatment of such clinical conditions. The object of the present invention is thus to provide further improved therapies for the treatment of acquired coagulopathies.

It was surprisingly found that a treatment of acquired coagulopathy with isolated PCC in combination with a pharmaceutical preparation comprising isolated FVIII and/or isolated vWF leads to a synergistically largely increased efficacy as compared to treatment with either PCC or a preparation comprising FVIII and vWF. The preparation to be combined with isolated PCC comprises FVIII and/or vWF and optionally other components which my also contribute to hemostasis. One embodiment of the invention is the combination of an isolated PCC with a medicament consisting essentially of FVIII and vWF.

"Isolated" in the sense of this invention means, that the respective coagulation factor or mixture of coagulation factors has been purified from either human plasma or, if produced recombinantly, from the culture medium. "Purified" in the sense of this invention means any type of purification which leads to a higher biological activity of said coagulation factor or mixture of coagulation factors per mg of total protein content or to a higher biological activity of said coagulation factor or mixture of coagulation factors per ml of liquid which is finally administered to the patient, as compared to the solution from which the respective coagulation factor or mixture of coagulation factors was obtained originally.

"Simultaneous use" in the sense of the invention means that the composition comprising isolated coagulation factors FII, FIX, FX and FVII and the composition comprising isolated FVIII and/or isolated vWF are mixed and then administered as a mixture to a patient.

"Separate use" in the sense of the invention means that the composition comprising isolated coagulation factors FII, FIX, FX and FVII and the composition comprising isolated FVIII and/or isolated vWF are administered both at the same time or separately one after the other, whereby the sequence of said administrations is not relevant.

"Sequential use" in the sense of the invention means than the composition comprising isolated coagulation factors FII, FIX, FX and FVII and the composition comprising isolated FVIII and/or isolated vWF are administered separately, whereby the sequence of said administration is not relevant, and whereby the time interval between both administrations is at most 2 days, preferentially at most 1 day and more preferentially at most 4 hours.

An animal model of a dilutional coagulopathy in hypothermic, normotensive pigs by fractionated blood withdrawal and substitution with hydroxyethyl starch (HES) was used to investigate efficacy of the proposed treatment. A trauma was induced by an incision into the spleen, blood loss and time to hemostasis were determined.

Substitution therapy was performed with Beriplex P/N® and either Helixate® or Humate P®. Beriplex P/N® is a prothrombin complex concentrate (PCC) comprising the vitamin K dependent coagulation factors II, VII, IX and X (Schulman, 2007). In addition Beriplex P/N® contains protein C and protein S. Helixate® consists of recombinant FVIII as the active constituent. Humate P®, is a product consisting essentially of FVIII as well as of vWF.

A dilutional coagulopathy was induced by the stepwise withdrawal of about 60% of the circulating blood volume and erythrocyte retransfusion. The decrease in circulating coagulation factors was monitored. The function of the clotting system was detected by thromboelastography and prothrombin time (PT). Platelet function was monitored by aggregation and adhesion. A substitution study consisted of the following groups: Untreated control group (no dilutional coagulopathy), dilutional coagulopathy without treatment, PCC, PCC+fibrinogen, PCC+vWF/FVIII, PCC+rec. FVIII, vWF/FVIII, rec. FVIIa, FIX/FX and PCC+vWF. Restoration of the coagulation system and bleeding after a spleen injury was determined.

The coagulopathy led to a decrease in coagulation factors to about 30% of the baseline concentration. Platelet numbers were decreased from about 400,000 to 100,000/µl, in addition, aggregation and adhesion were impaired. PCC could substitute the lacking prothrombin factors (II, VII, IX and X) and improved coagulation. After spleen injury PCC significantly reduced time to hemostasis and reduced blood loss when compared to the dilutional control. On the other hand vWF/FVIII alone did not change the outcome of the study, nor did the treatment with FIX or respectively FVIIa. In contrast the combination of PCC with either FVIII or vWF or vWF/FVIII significantly reduced time to hemostasis and blood loss to nearly normal values. This shows that the combination of FVIII/ and/or vWF with PCC is significantly more effective than the monotherapy with PCC alone, indicating a synergistic effect.

In the group treated with vWF/FVIII in addition the adhesion capacity of platelets was significantly increased, indicating that also the impaired platelet function could be normalized.

In recent years attempts have been made to substitute in bleeding conditions with a single component of the prothrombin complex namely the activated form of FVII which is available as rec. FVIIa (for a review see Holcomb, 2005). Rec. FVIIa is able to directly bind to the activated platelet and to initiate the conversion of FX to FXa while bypassing the tenase (FIXa/VIIIa) pathway. This is the basis for the well-known efficacy of rec. FVIIa in treating hemophilia A and B patients with inhibitors to FVIII or FIX (Habermann et al., 2004). While hemophilia inhibitor patients have enough FX and prothrombin, the situation in a patient with a severe dilution coagulopathy is different. If FX decreases under a critical level rec. FVIIa will lack its substrate. A multicomponent therapeutic agent such as PCC can offer advantages in a situation of a general decrease in coagulation factors. PCC substituted for the proteins of the prothrombin complex, factors II, VII, IX and X. The first and foremost task of the coagulation system is to assure thrombin generation. Thrombin has multiple functions in the coagulation system: the formation of fibrin from fibrinogen, the activation of the cofactors V and VIII, the activation of FXIII and the activation of platelet via the thrombin receptor. The generation of thrombin requests sufficient prothrombin (FII) as a substrate from the prothrombinase complex which contains the activated form of FX as the acting serine protease. The activated form of FIX is the enzyme of the tenase complex, which together with FVIII converts FX to FXa. It is tempting to believe that all four enzymes of the prothrombin complex are indispensable to generate thrombin. Our data suggest that it is mandatory to supply enough prothrombin complex factors to initiate the thrombin burst and that the combination of PCC with FVIII and/or vWF comprising compositions effectively reconstitutes the impaired coagulation cascade and significantly shortens time to hemostasis.

The invention relates to two pharmaceutical compositions which, when combined show a synergistic effect.

The first pharmaceutical composition comprising isolated coagulation factors FII, FIX, FX and FVII to be used in the present invention and the second pharmaceutical composition comprising isolated FVIII and/or isolated vWF, can be manufactured as two independent compositions, which can be separately sold, or can be combined in one kit as separate pharmaceutical compositions or can be manufactured to be comprised in one single pharmaceutical composition as a mixture of all components.

The invention therefore relates to a composition comprising isolated coagulation factors FII, FIX, FX and FVII and a composition comprising isolated FVIII and/or isolated vWF for simultaneous, separate or sequential use in a method of treatment of acquired bleeding.

The invention further relates to the use of a composition comprising isolated coagulation factors FII, FIX, FX and FVII and a composition comprising isolated FVIII and/or vWF for the manufacture of pharmaceutical preparations for simultaneous, separate or sequential use in the therapy of acquired coagulopathies.

A further aspect of the invention is the use of a composition comprising isolated coagulation factors FII, FIX, FX and FVII and a composition comprising isolated FVIII and/or vWF for the manufacture of a combined pharmaceutical preparation for simultaneous, separate or sequential use in the therapy of acquired coagulopathies. All compositions of the invention comprise coagulation factors which have not been activated.

In a preferred embodiment of the invention the isolated coagulation factors FII, FIX, FX and FVII are a prothrombin complex concentrate (PCC) derived from human blood or a PCC reconstituted from recombinantly expressed coagulation factors wherein the ratios of antigen and activity of said recombinantly expressed coagulation factors FVII, FIX, FX and FVII correspond to PCCs derived from blood.

Prothrombin complex concentrate (PCC) in the meaning of the present invention comprises a combination of coagulation factors FII, FIX, FX and FVII. PCC may also contain protein C and protein S.

Isolated PCC compositions as listed in Table I are encompassed by the present invention. Fresh frozen plasma contains per definition 1 IU/ml, thus the concentration of the prothrombin complex factors are enriched several fold in PCC.

Isolated PCC in the sense of the invention encompasses PCC compositions in which each individual coagulation factor is present in a liquid or if stored lyophilized in the liquid after reconstitution prior to injection by at least a factor of 2.5 as compared to its concentration in blood.

TABLE 1

Compositions of preferred PCCs

|  | Most preferred | More preferred | Preferred |
|---|---|---|---|
| a) essential components | | | |
| Factor II | 20-48 IU/ml | 10-90 IU/ml | 5-180 IU/ml |
| Factor VII | 10-25 IU/ml | 5-50 IU/ml | 2.5-100 IU/ml |
| Factor IX | 20-35 IU/ml | 10-60 IU/ml | 5-120 IU/ml |
| Factor X | 22-60 IU/ml | 10-120 IU/ml | 5-240 IU/ml |
| b) optional components | | | |
| Protein C | 15-45 IU/ml | 8-90 IU/ml | 4-180 IU/ml |
| Protein S | 13-26 IU/ml | 6-50 IU/ml | 3-100 IU/ml |

Functional coagulation factor II (FII) displays the biological activity of prothrombin, which represents the inactive proenzyme of thrombin (FIIa). After activation of the coagulation cascade the conversion of prothrombin to thrombin takes place, the latter multiple activating functions in the coagulation system include among others the conversion of fibrinogen to fibrin, activation of coagulation factor XIII (FVIII) to activated coagulation factor XIII (XIIIa), activation of FV and FVIII to FVa and VIIIa, platelet activation after partial proteolysis of the thrombin receptor.

Functional coagulation factor IX (FIX) displays the biological activity of inactive FIX, which is converted upon coagulation activation to the active FIXa. FIXa forms a complex with its coenzyme FVIIIa and represents the tenase complex, which cleaves the inactive FX to its active form FXa.

Functional coagulation factor X (FX) displays the biological activity of inactive FX which is converted to active FXa after coagulation activation. FXa forms a complex with its coenzyme FVa which represents the prothrombinase complex which cleaves the inactive prothrombin (FII) into the active thrombin (FIIa).

Functional coagulation factor FVII (FVII) displays the biological activity of inactive FVII which is converted during the activation of coagulation to FVIIa. FVIIa together with tissue factor converts the inactive FX to the active FXa. Additionally FVIIa can convert inactive FIX to active FIXa.

Functional coagulation factor VIII (FVIII) displays the biological activity of the coenzyme FVIII, which is converted to FVIIIa during coagulation activation. FVIIIa is the coenzyme for the protease FIXa and forms a complex with FIXa. The FVIIIa/FIXa complex cleaves the inactive FX to form activated FXa.

Isolated FVIII in the sense of the invention encompasses FVIII compositions in which FVIII is present in a liquid or if stored lyophilized in the liquid after reconstitution prior to injection in a concentration which is by at least a factor of 2.5 higher than the concentration of FVIII in blood.

Functional von Willebrand factor (vWF) displays the biological activity of vWF a large multimeric protein with multiple binding sites responsible for positioning thrombocytes to the site of injury. VWF binds to the thrombocyte via its A1 domain and to the collagen at the site of injury with its A3 domain. It thus mediates thrombocyte adhesion. Additionally thrombocyte aggregation is induced by binding of vWF to the αIIb/β3 receptor and vWF stabilizes the circulating FVIII.

Isolated vWF in the sense of the invention encompasses vWF compositions in which vWF is present in a liquid or if stored lyophilized in the liquid after reconstitution prior to injection in a concentration which is by at least a factor of 2.5 higher than the concentration of vWF in blood.

The activity of the coagulation factors discussed above can be measured according to L. Thomas: Clinical Laboratory Diagnostics, TH-Books, Frankfurt, 1998, Chapter 17.

Preferred compositions of a combination preparation comprising FVIII and vWF are indicated in table 2:

TABLE 2

Compositions of preferred combination preparations comprising FVIII and vWF

|  | Most preferred | More Preferred | Preferred |
|---|---|---|---|
| Factor VIII | 20-40 IU/ml | 10-60 IU/ml | 5-120 |
| VWF | 50-100 IU/ml | 25-160 IU/ml | 13-320 |

TABLE 3

Preferred combinations between PCC and FVIII/vWF
($X_n$ represents respectively one out of nine preferred combinations of a preferred PCC concentration and a preferred FVIII/vWF concentration)

| Preferred FVIII/vWF concentration | Preferred PCC concentration (based on FIX units) | | |
|---|---|---|---|
| (based on FVIII units) | Most preferred 20-35 IU/ml | More preferred 10-60 IU/ml | Preferred 5-120 IU/ml |
| Most preferred 20-40 IU/ml | $X_1$ | $X_2$ | $X_3$ |
| More preferred 10-60 IU/ml | $X_4$ | $X_5$ | $X_6$ |
| Preferred 5-120 IU/ml | $X_7$ | $X_8$ | $X_9$ |

The coagulation factors used in said pharmaceutical compositions can be obtained from human plasma or serum or recombinantly. "Coagulation factors" as used in the present invention comprise proteins that have the amino acid sequence of native human coagulation factors. Also comprised are coagulation factors with a slightly modified amino acid sequence, for instance, a modified N-terminal end including N-terminal amino acid deletions or additions so long as those proteins substantially retain the activity of the coagulation factors. "The coagulation factors" within the above definition also comprise natural allelic variations that may exist and occur from one individual to another. "The coagulation factors" within the above definition further comprise variants of such coagulation factors. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, e.g. addition of a methionine residue at the N-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, (6) aromatic amino acids. Examples of such conservative substitutions are shown in the following table.

| (1) | Alanine | Glycine | | |
|---|---|---|---|---|
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

"Functional coagulation factors" as used in this invention comprise coagulation factor molecules displaying biological activity either in solution and/or on cellular surfaces as described above.

The term "recombinant" means, for example, that the variant has been produced in a host organism by genetic engineering techniques.

The host cells of the invention may be employed in a method of producing human coagulation factors. The method comprises:

a) culturing host cells of the invention under conditions such that one or more human coagulation factors is/are expressed; and
b) optionally recovering one or more human coagulation factors from the host cells or from the culture medium.

Degree and location of glycosylation or other post-translation modifications may vary depending on the chosen host cells and the nature of the host cellular environment. When referring to specific amino acid sequences, posttranslational modifications of such sequences are encompassed in this application.

The production of recombinant proteins at high levels in suitable host cells, requires the assembly of the above-mentioned modified cDNAs into efficient transcriptional units together with suitable regulatory elements in a recombinant expression vector, that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the coagulation factors. Preferably this cell line should be an animal cell-line of vertebrate origin in order to ensure correct folding, Gla-domain synthesis, disulfide bond formation, asparagine-linked glycosylation, O-linked glycosylation, and other post-translational modifications as well as secretion into the cultivation medium. Examples of other post-translational modifications are hydroxylation and proteolytic processing of the nascent polypeptide chain. Examples of cell lines that can be used are monkey COS-cells, mouse L-cells, mouse C127-cells, hamster BHK-21 cells, human embryonic kidney 293 cells, and preferentially hamster CHO-cells. Due to their complex post-translational modifications recombinant coagulation factors are preferably expressed in human cell lines.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene, which may function as a dominant selectable marker in these cells in order to facilitate the isolation of specific cell clones, which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated into the genome of the host cell, frequently resulting in a tight physical linkage between the different transcription units.

Other types of selectable marker genes, which can be used together with the cDNA of the desired protein, are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the coagulation factor cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant proteins The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody, which is immobilised on a solid support. After desorption, the protein can be further purified by a variety of chromatographic techniques based on the above properties.

It is preferred to purify the coagulation factors of the present invention, irrelevant whether produced by recombinant means or obtained from human plasma, to 60% purity, more preferably ≥80% purity, and particularly preferred is a pharmaceutically pure state that is greater than 95% pure with respect to contaminating macromolecules, particularly other proteins and nucleic acids, and free of infectious and pyrogenic agents.

The coagulation factors as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", $3^{rd}$ edition, Kibbe et al., Pharmaceutical Press (2000)). In particular, the pharmaceutical composition comprising the polypeptide variant of the invention may be formulated in lyophilized or stable soluble form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially the compositions of the invention are administered systemically. For systemic use, the coagulation factors of the invention are formulated for parenteral (e.g. intravenous, subcutaneous, intramuscular, intraperitoneal, intracerebral, intrapulmonar, intranasal or transdermal or vaginal) or enteral (e.g., oral, or rectal) delivery according to conventional methods. The most preferential routes of administration are intravenous and subcutaneous administration. The formulations can be administered continuously by infusion or by bolus injection. Some formulations encompass slow release systems.

The coagulation factors of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The coagulation factors of the present invention can be used to treat bleedings, including:

All types of trauma, (blunt or penetrating, leading to severe hemorrhage either from a single organ, a bone fraction or from polytrauma.
Bleeding during surgical procedures including peri- or postoperative hemorrhage.
Bleeding due to cardiac surgery including patients undergoing extracorporal circulation and hemodilution in pediatric cardiac surgery
Intracerebral hemorrhage, subarachnoid hemorrhage, sub- or epidural bleeding
Bleedings due to blood loss and hemodilution, by non-plasmatic volume substitution leading to reduced levels of coagulation factors in affected patients
Bleedings due to disseminated intravascular coagulation (DIC) and a consumption coagulopathy
Thrombocyte dysfunctions, depletion and coagulopathies
Bleeding due to liver cirrhosis, liver dysfunction and fulminant liver failure.
Liver biopsy in patients with liver disease
Bleeding after liver and other organ transplantations
Bleeding from gastric varices and peptic ulcer bleeding
Gynecological bleedings as dysfunctional uterine bleeding (DUB), premature detachment of the placenta
Periventricular hemorrhage in low birth weight children
Post partum haemorrhage
Fatal distress of newborns
Bleeding associated with burns
Bleeding associated with amyloidosis
Hematopoietic stem cell transplantation associated with platelet disorder
Bleedings associated with malignancies
Infections with hemorrhaging viruses
Bleeding associated with pancreatitis

FIGURES

FIG. 1: Blood Loss (An animal model of a dilutional coagulopathy in hypothermic, normotensive pigs by fractionated blood withdrawal and substitution with hydroxyethyl starch (HES) was used to investigate efficacy of the proposed treatment. A trauma was induced by an incision into the spleen, blood loss was determined. Substitution therapy was performed with Beriplex P/N® and either Helixate® or Humate P®. Beriplex P/N® is a prothrombin complex concentrate (PCC) comprising the vitamin K dependent coagulation factors II, VII, IX and X (Schulman, 2007). In addition Beriplex P/N® contains protein C and protein S. Helixate® consists of recombinant FVIII as the active constituent. Humate P®, is a product consisting essentially of FVIII as well as of vWF.)

EXAMPLE 1

Pig Model of Dilutional Coagulopathy and Spleen Trauma

Pigs were fasted overnight but had free access to water. Animals were premedicated intramuscularly with a mixture of 2 mg/kg Azaperone (Stresnil/Janssen), 15 mg/kg Ketamin (Ketavet/Pfitzer) and 0.02 mg/kg Atropinsulfate (Atropinsulfate, B. Braun). Anesthesia was induced by 10 mg/kg Thiopental-sodium via an ear vein. Pigs were intubated and respirated via a Heyer Access ventilator. Inhalation anaesthesia was maintained by Isoflurane (Forene, Abbott), the concentration was 1-2%, dependent on the status of anaesthesia.

A 1.4×2.1 mm catheter was advanced into the A. carotis for the collection of blood samples and a 0.5×0.9 mm catheter was placed into the A. femoralis for the continous blood pressure measurements. A 1.4×2.1 mm catheter was introduced into the V. jugularis externa for blood withdrawal and administration of erythrocytes, plasma expander and test substances. Basic fluid requirement was achieved by intravenous administration of Ringer Lactate (4 mL/kg×h). Body temperature was measured by a rectal thermometer.

After a period of 30 min. to allow the stabilization of the circulation baseline haemodynamic, coagulation and hematological parameters were assessed (t=0). Subsequently a hypothermic, normotensive dilution coagulopathy was induced by stepwise withdrawal of blood. For the reinfusion of erythrocytes blood was centrifuged (800×g, 10 minutes), red cells were resuspended in NaCl to achieve the initial volume. After resuspension erythrocytes were centrifuged again, resuspended in the half of the initial volume in Ringer-Lactate and reinfused to the animal. After withdrawal of about 65-70% of arterial blood, 6% Hydroxyethyl starch (HES, Infukoll 6%, Schwarz Pharma) at room temperature were infused intravenously.

After HES infusion blood samples were taken again (t=80 min.) and the animal was allowed to stabilize for 40 minutes. The third blood sample was withdrawn (t=120 min.) and a standardized spleen incision (8 cm length, 1 cm deep) was performed by a scalpel blade.

Blood was suctioned out of the abdomen and total blood loss and time to hemostasis was determined. Test substances were infused shortly before the spleen incision.

Pigs undergoing the dilution procedure had a mild hypothermia, the temperature fell from 38.5° C. to 36° C. Blood pressure decreased after blood withdrawal, but was back to baseline values after the substitution with HES and remained on a constant level until the spleen injury was performed. Prior to spleen injury the hematocrit had decreased to 60% of its baseline value.

Substitution Therapy

The following compounds were used for substitution therapy. Beriplex® P/N (CSL Behring, Marburg, Germany) is a virus inactivated human prothrombin complex concentrate (PCC). It contains the human plasma coagulation factors II, VII, IX and X as well as protein C and S. Humate® P (CSL Behring) is a complex from human plasma coagulation factor VIII and von Willebrandt factor (vWF). Haemocomplettan® (CSL Behring, Marburg, Germany) is a fibrinogen concentrate from human plasma. NovoSeven® (recombinant factor VIIa) was from NovoNordisk. Helixate® (CSL Behring) is a recombinant FVIII. FIXP Behring (CSL Behring) is a FIX and FX containing product from human plasma. VWF was purified from human plasma.

Treatment groups were as follows: 1: normal pigs (negative control, n=5), 2: dilution control (no treatment) (n=16), 3: Beriplex P/N® 35 U/kg (Factor IX units), 4: Beriplex P/N® 35 U/kg+Haemcomplettan® 250 mg/kg, 5: Beriplex PIN® 20-35 U/kg+Humate® 40 U/kg (Factor VIII units) (n=14) 6: Humate® 40 U/kg (n=5). 7. NovoSeven® 180 µg/kg (n=5). 8. Beriplex® P/N 30 U/kg+Helixate® (rec. FVIII) 40 U/kg (n=3), 9. FIX P+30 U/kg (Factor IX units) (n=3), 10. Beriplex® P/N+human plasma vWF 90 U/kg (vWF units), (n=3)

TABLE 4

Synergistic effect of a combination therapy using PCC and vWF Results from a Spleen Incision Trauma in Pigs: Time to Hemostasis and Blood loss

| Treatment | Time to hemostasis (min.) | Blood loss (mL) |
| --- | --- | --- |
| 1. Negative control (n = 5) | 20.6 ± 7.8 | 83.2 ± 63.5 |
| 2. Dilution control (n = 16) | 86.7 ± 24.1 | 657.5 ± 298.5 |
| 3. Beriplex ® P/N (n = 5) | 37.6 ± 13.6<br>2-3 p < 0.001 | 405.8 ± 223.1 |
| 4. Beriplex ® P/N + Haemocomplettan ®P (n = 5) | 39.6 ± 11.9<br>2-4 p < 0.001 | 334.5 ± 137.7<br>2-4 p < 0.05 |
| 5. Beriplex ® P/N + Haemate ® P (n = 14) | 29.6 ± 7.1<br>2-5 p < 0.0001 | 190.4 ± 85.0<br>2-5 p < 0.00011 |
| 6. Haemate ® P (n = 5) | 68.8 ± 27.8 | 471.0 ± 234.6 |
| 7. NovoSeven (n = 5) | 91.8 ± 26.2 | 729 ± 265 |
| 8. Beriplex P/N + rec. FVIII (Helixate) (n = 3) | 33.7 ± 4.6<br>2-8 p < 0.01 | 178 ± 58.8<br>2-8 p < 0.02 |
| 9. FIX + FX (n = 3) | 115.0 ± 7.1 | 953 ± 232 |
| 10. Beriplex P/N + human plasma vWF | 27.7 ± 3.1<br>2-10 p < 0.001 | 257.3 ± 42.6<br>2-10 p < 0.05 |

The invention claimed is:

1. A kit for treatment of acquired coagulopathy in a patient comprising a first pharmaceutical composition comprising isolated coagulation factors FII, FIX, FX and FVII and a second, separate pharmaceutical composition comprising isolated FVIII and/or isolated vWF.

2. The kit according to claim 1, wherein the isolated coagulation factors FII, FIX, FX and FVII of the first composition are a prothrombin complex concentrate (PCC) derived from human blood.

3. The kit according to claim 1, wherein the isolated coagulation factors FII, FIX, FX and FVII of the first composition are recombinantly expressed, and wherein the recombinantly expressed coagulation factors are combined such that the ratios of antigen and activity of said recombinantly expressed coagulation factors correspond to PCCs derived from human blood.

4. The kit according to claim 1, wherein the isolated coagulation factor(s) FVIII and/or vWF of the second composition are derived from human blood.

5. The kit according to claim 1, wherein the isolated coagulation factor(s) FVIII and/or vWF of the second composition are recombinantly expressed.

6. The kit according to claim 1, wherein the first composition comprises 5-180 IU/ml FII, 2.5-100 IU/ml FVII, 5-120 IU/ml FIX, and 5-240 IU/ml FX, and the second composition comprises 5-120 IU/ml FVIII and/or 13-320 IU/ml vWF.

7. A method of treating acquired coagulopathy comprising administering to a patient in need thereof an effective amount of the kit according to claim 1.

8. The method according to claim 7, wherein the acquired coagulopathy is one or more of bleeding due to trauma; bleeding during surgical procedures; bleeding due to cardiac surgery; intracerebral hemorrhage; subarachnoid hemorrhage; sub- or epidural bleeding; bleeding due to blood loss and hemodilution; bleeding due to disseminated intravascular coagulation (DIC) and a consumption coagulopathy; thrombocytopenia; thrombocyte dysfunction; bleeding due to liver cirrhosis, liver dysfunction and/or fulminant liver failure; bleeding due to liver biopsy in a patient with liver disease; bleeding after organ transplantation; bleeding from gastric varices; peptic ulcer bleeding; gynecological bleeding; periventricular hemorrhage in a low birth weight child; post partum haemorrhage; bleeding due to fatal distress of a newborn; bleeding associated with a burn; bleeding associated with amyloidosis; bleeding due to hematopoietic stem cell transplantation associated with a platelet disorder; bleeding associated with malignancy; bleeding due to infection with a hemorrhagic virus; and bleeding associated with pancreatitis.

9. The method according to claim 8, wherein the acquired coagulopathy is bleeding due to trauma.

10. The method according to claim 7, wherein the first and second compositions of the kit are administered simultaneously.

11. The method according to claim 7, wherein the first and second compositions of the kit are administered separately.

12. The method according to claim 7, wherein the first and second compositions of the kit are administered sequentially.

13. The method according to claim 7, wherein the first composition of the kit comprises 5-180 IU/ml FII, 2.5-100 IU/ml FVII, 5-120 IU/ml FIX, and 5-240 IU/ml FX, and the second composition of the kit comprises 5-120 IU/ml FVIII and/or 13-320 IU/ml vWF.

14. A method of treating acquired coagulopathy comprising administering to a patient in need thereof an effective amount of a first pharmaceutical composition comprising isolated coagulation factors FII, FIX, FX, and FVII, and of a second, separate pharmaceutical composition comprising isolated FVIII and/or isolated vWF.

15. The method according to claim 14, wherein the acquired coagulopathy is one or more of bleeding due to trauma; bleeding during surgical procedures; bleeding due to cardiac surgery; intracerebral hemorrhage; subarachnoid hemorrhage; sub- or epidural bleeding; bleeding due to blood loss and hemodilution; bleeding due to disseminated intravascular coagulation (DIC) and a consumption coagulopathy; thrombocytopenia; thrombocyte dysfunction; bleeding due to liver cirrhosis, liver dysfunction and/or fulminant liver failure; bleeding due to liver biopsy in a patient with liver disease; bleeding after organ transplantation; bleeding from gastric varices; peptic ulcer bleeding; gynecological bleeding; periventricular hemorrhage in a low birth weight child; post partum hemorrhage; bleeding due to fatal distress of a newborn; bleeding associated with a burn; bleeding associated with amyloidosis; bleeding due to hematopoietic stem cell transplantation associated with a platelet disorder; bleeding associated with malignancy; bleeding due to infection with a hemorrhagic virus; and bleeding associated with pancreatitis.

16. The method according to claim 15, wherein the acquired coagulopathy is bleeding due to trauma.

17. The method according to claim 14, wherein the first and second compositions are administered simultaneously.

18. The method according to claim 14, wherein the first and second compositions are administered separately.

19. The method according to claim 14, wherein the first and second compositions are administered sequentially.

20. The method according to claim 14, wherein the first composition comprises 5-180 IU/ml FII, 2.5-100 IU/ml FVII, 5-120 IU/ml FIX, and 5-240 FX, and the second composition comprises 5-120 IU/ml FVIII and/or 13-320 IU/ml vWF.

* * * * *